United States Patent
Schiffrin et al.

(10) Patent No.: US 9,763,898 B2
(45) Date of Patent: Sep. 19, 2017

(54) NUTRITIONAL COMPOSITION FOR PROMOTING MUSCULOSKELETAL HEALTH IN PATIENTS WITH INFLAMMATORY BOWEL DISEASE (IBD)

(71) Applicant: NESTEC S.A., Vevey (CH)

(72) Inventors: Eduardo Schiffrin, Crissier (CH); Viral Brahmbhatt, Geneva (CH); Francois-Pierre Martin, Vuisternens-devant-Romont (CH); Jalil Benyacoub, Epalinges (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 15/368,167

(22) Filed: Dec. 2, 2016

(65) Prior Publication Data

US 2017/0079935 A1  Mar. 23, 2017

Related U.S. Application Data

(63) Continuation of application No. 14/414,760, filed as application No. PCT/EP2013/065948 on Jul. 30, 2013, now Pat. No. 9,561,194.

(30) Foreign Application Priority Data

Jul. 31, 2012 (EP) .................................. 12178573

(51) Int. Cl.

| | | |
|---|---|---|
| *A61K 31/122* | (2006.01) | |
| *A23L 1/27* | (2006.01) | |
| *A23L 1/30* | (2006.01) | |
| *A23L 1/302* | (2006.01) | |
| *A23L 1/303* | (2006.01) | |
| *A23L 1/304* | (2006.01) | |
| *A23L 1/305* | (2006.01) | |
| *A23L 1/308* | (2006.01) | |
| *A23L 2/38* | (2006.01) | |
| *A23L 2/66* | (2006.01) | |
| *A61K 31/015* | (2006.01) | |
| *A61K 31/07* | (2006.01) | |
| *A61P 3/02* | (2006.01) | |
| *A61K 31/14* | (2006.01) | |
| *A61K 31/197* | (2006.01) | |
| *A61K 31/20* | (2006.01) | |
| *A61K 31/355* | (2006.01) | |
| *A61K 31/375* | (2006.01) | |
| *A61K 31/4188* | (2006.01) | |
| *A61K 31/4415* | (2006.01) | |
| *A61K 31/455* | (2006.01) | |
| *A61K 31/51* | (2006.01) | |
| *A61K 31/519* | (2006.01) | |

(Continued)

(52) U.S. Cl.
CPC ............. *A61K 31/122* (2013.01); *A23L 2/38* (2013.01); *A23L 2/66* (2013.01); *A23L 5/40* (2016.08); *A23L 33/10* (2016.08); *A23L 33/12* (2016.08); *A23L 33/135* (2016.08); *A23L 33/15* (2016.08); *A23L 33/155* (2016.08); *A23L 33/16* (2016.08); *A23L 33/175* (2016.08); *A23L 33/19* (2016.08); *A23L 33/21* (2016.08); *A23L 33/30* (2016.08); *A23L 33/40* (2016.08); *A61K 31/015* (2013.01); *A61K 31/07* (2013.01); *A61K 31/14* (2013.01); *A61K 31/197* (2013.01); *A61K 31/20* (2013.01); *A61K 31/202* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/59* (2013.01); *A61K 31/714* (2013.01); *A61K 33/00* (2013.01); *A61K 33/04* (2013.01); *A61K 33/06* (2013.01); *A61K 33/16* (2013.01); *A61K 33/18* (2013.01); *A61K 33/20* (2013.01); *A61K 33/24* (2013.01); *A61K 33/26* (2013.01); *A61K 33/30* (2013.01); *A61K 33/32* (2013.01); *A61K 33/34* (2013.01); *A61K 33/42* (2013.01); *A61K 38/1709* (2013.01); *A61K 45/06* (2013.01); *A23V 2002/00* (2013.01); *A23V 2200/00* (2013.01)

(58) Field of Classification Search
None
See application file for complete search history.

(56) References Cited

U.S. PATENT DOCUMENTS

2005/0054724 A1  3/2005  Mustad et al.
2005/0256031 A1  11/2005  Hageman et al.

FOREIGN PATENT DOCUMENTS

EP   0852913   7/1998

OTHER PUBLICATIONS

Kuwabara et al. "High prevalence of vitamin K and D deficiency and decreased BMD in inflammatory bowel disease" Osteoporos Int., 2009, vol. 20, pp. 935-942.

(Continued)

*Primary Examiner* — Sue Liu
*Assistant Examiner* — Frank Choi
(74) *Attorney, Agent, or Firm* — K&L Gates LLP (57) ABSTRACT

A nutritional composition promotes musculoskeletal health in patients with inflammatory bowel disease. The nutritional composition contains casein protein, vitamin D, alpha-linolenic acid, and vitamin K in a ratio of vitamin K1:vitamin K2 between 3:1 to 1:3 and the vitamin K providing between 3.5-20 μg/100 cal of the nutritional composition. A pharmaceutical formulation, a nutritional formulation, a tube-feed formulation, a dietary supplement, a functional food, a beverage product or a combination thereof comprising the (Continued)

nutritional composition is also disclosed. A method for improving musculoskeletal health is also disclosed.

9 Claims, 2 Drawing Sheets (51) Int. Cl.

| | |
|---|---|
| A61K 31/525 | (2006.01) |
| A61K 31/59 | (2006.01) |
| A61K 31/714 | (2006.01) |
| A61K 33/00 | (2006.01) |
| A61K 33/04 | (2006.01) |
| A61K 33/06 | (2006.01) |
| A61K 33/16 | (2006.01) |
| A61K 33/18 | (2006.01) |
| A61K 33/20 | (2006.01) |
| A61K 33/24 | (2006.01) |
| A61K 33/26 | (2006.01) |
| A61K 33/30 | (2006.01) |
| A61K 33/32 | (2006.01) |
| A61K 33/34 | (2006.01) |
| A61K 33/42 | (2006.01) |
| A61K 38/17 | (2006.01) |
| A61K 45/06 | (2006.01) |
| A23L 5/40 | (2016.01) |
| A23L 33/00 | (2016.01) |
| A23L 33/10 | (2016.01) |
| A23L 33/12 | (2016.01) |
| A23L 33/135 | (2016.01) |
| A23L 33/15 | (2016.01) |
| A23L 33/155 | (2016.01) |
| A23L 33/16 | (2016.01) |
| A23L 33/175 | (2016.01) |
| A23L 33/19 | (2016.01) |
| A23L 33/21 | (2016.01) |
| A61K 31/202 | (2006.01) |

(56) References Cited

OTHER PUBLICATIONS

Iwamoto et al. "High-dose vitamin K supplementation reduces fracture incidence in postmenopausal women: a review of the literature" Nutrition Research, vol. 29, 2009, pp. 221-228.

Nieves, Skeletal effects of nutrients and nutraceuticals, beyond calcium and Vitamin D, Osteoporos Int. (2013), vol. 24, pp. 771-786.

NUTRITIONAL COMPOSITION FOR PROMOTING MUSCULOSKELETAL HEALTH IN PATIENTS WITH INFLAMMATORY BOWEL DISEASE (IBD)

PRIORITY CLAIM

The present application is a continuation of U.S. patent application Ser. No. 14/414,760 filed Jan. 14, 2015, which is a National Stage of International Application No. PCT/EP13/065948 filed Jul. 30, 2013, which claims priority to European Patent Application No. 12178573.7 filed Jul. 31, 2012, the entire contents of which are incorporated herein by reference.

FIELD OF THE INVENTION

The present disclosure is related to a nutritional composition, in particular a nutritional composition for patients with inflammatory bowel disease. The present disclosure also relates to a method for improving musculoskeletal health in patients, in particular patients with inflammatory bowel disease.

BACKGROUND

Inflammatory bowel disease refers to a group of diseases that involves an inflammation of the gastrointestinal tract.

Crohn's disease is an example of an inflammatory bowel disease. Crohn's disease can affect the entire gastrointestinal tract from the mouth to the anus.

An exact cause of Crohn's disease is unknown. Crohn's disease is believed to be caused by a combination of genetic, non-genetic or environmental factors (e.g. infections) that interact with the body's immune system and this affects the gastrointestinal tract.

Crohn's disease is a chronic inflammatory disorder in which the body's immune system mistakenly attacks and destroys the healthy tissue of the gastrointestinal tract. The signs and symptoms of Crohn's disease involve chronic recurring periods of flare-ups and remission.

Crohn's disease can result in gastrointestinal, extra-intestinal and systemic complications. Gastrointestinal complications can include diarrhea, abdominal pain, fever and rectal bleeding. Extra-intestinal complications include problems with the eyes, bones, skin abnormalities and blood abnormalities. Furthermore extra-intestinal complications of Crohn's disease leads to reduced bone density causing osteoporosis or increased bone Softening causing osteomalacia. Systemic complications associated with Crohn's disease include growth retardation in children, weight loss due to decreased food intake and malabsorption of carbohydrates or lipids which further exacerbate weight loss.

There is no single cure for Crohn's disease. Where remission of Crohn's disease is possible, relapse can be prevented and symptoms controlled with medication, lifestyle changes, intervention with nutritional compositions and in some cases surgery.

Treatment of Crohn's disease is only possible when the symptoms are active. Treatment of Crohn's disease usually involves first treating the acute problem and then maintaining remission.

There is a need to provide a nutritional composition that can correct metabolic changes in patients with Crohn's disease and prevent and correct Crohn's disease associated alterations in patients with Crohn's disease.

There is a need to be able to monitor patients with Crohn's disease to be able to predict a likelihood of a relapse and remission of the effects of Crohn's disease prior to its occurrence during the remission period. The monitoring of patients with Crohn's disease in this manner is achieved with so called biomarkers. Biomarkers allow a possibility of an early nutritional intervention to maintain a state of remission. Thus, it is desirable to identify biomarkers in patients with Crohn's disease which can be used a diagnostic tool.

Nutritional compositions are known for providing a sole nutritional composition and/or supplemental nutritional composition to patients with inflammatory bowel disease (e.g. Crohn's disease). The nutritional compositions are a primary therapy for inflammatory bowel disease (e.g. Crohn's disease). The nutritional compositions may enable inflammatory activity to be controlled and may enable the patients to be kept in a state of remission.

A nutritional composition—Modulen IBD manufactured by Nestle is known. Modulen IBD is used for patients with inflammatory bowel disease (e.g. Crohn's disease). Modulen IBD is known to contain vitamin K in an amount of 27 µg/100 g. Modulen IBD is known to contain vitamin D in an amount of 4.9 µg/100 g. Modulen IBD is known to contain alpha-linolenic acid in an amount of 0.2 g/100 g. Modulen IBD is a casein-protein based composition. The casein in Modulen IBD provides an anti-inflammatory cytokine-transforming growth factor-$\beta_2$ The transforming growth factor-$\beta_2$ has been shown to induce remission in children with active inflammatory bowel disease (e.g. Crohn's disease). The transforming growth factor-$\beta_2$ promotes mucosal healing of the gastrointestinal tract as it controls inflammatory activity.

Furthermore the transforming growth factor-has immunomodulatory properties.

WO2011/031601 discloses a nutritional composition and a method of making and using the nutritional composition. The nutritional composition includes exogenous vitamin K2. The nutritional composition may further include an additional component selected from phosphorus, magnesium, zinc, iron, copper, manganese, calcium, vitamin D, osteopontin and combinations thereof.

SUMMARY

There is a need to provide a nutritional composition which promotes musculoskeletal health in patients with inflammatory bowel disease (e.g. Crohn's disease).

There is a need to provide a nutritional composition which restores the metabolic profile in patients with inflammatory bowel disease (e.g. Crohn's disease).

The patients can be pediatric or teenaged patients. A pediatric patient is a patient in the age between 0 and 18 years, 0 and 17 years, or 0 and 17 years. An age of 0 refers to the time of birth independent of whether the birth was premature or not. A teenaged patient is a patient in the age between 13 and 19, 13 and 18, or 13 and 17 years.

In a first aspect the present disclosure relates to a nutritional composition. The nutritional composition comprises acid casein protein, vitamin K in a ratio of vitamin K1:K2 being between 3:1 to 1:3 and the vitamin K present in an amount of between 17.5 to 100 µg/100 g of the nutritional composition, vitamin D present in an amount of between 2.5 to 75 µg/100 g of the nutritional composition; and n6/n3 fatty acids in a ratio of n6:n3 fatty acids of between 5:1 to 1:5.

In a further aspect the present disclosure relates to a pharmaceutical formulation, a nutritional formulation, a tube-feed formulation, a dietary supplement, a functional food, a beverage product or a combination thereof comprising a nutritional composition that comprises acid casein protein, vitamin K in a ratio of vitamin K1:K2 being between 3:1 to 1:3 and the vitamin K present in an amount of between 17.5 to 100 µg/100 g of the nutritional composition, vitamin D present in an amount of between 2.5 to 75 µg/100 g of the nutritional composition; and n6/n3 fatty acids in a ratio of n6:n3 fatty acids of between 5:1 to 1:5.

In a further aspect the present disclosure relates to a method of improving musculoskeletal health in pediatric patients. The method comprises administering to pediatric patients in need of same a nutritional composition that comprises acid casein protein, vitamin K in a ratio of vitamin K1:K2 being between 3:1 to 1:3 and the vitamin K present in an amount of between 17.5 to 100 µg/100 g of the nutritional composition, vitamin D present in an amount of between 2.5 to 75 µg/100 g of the nutritional composition; and n6/n3 fatty acids in a ratio of n6:n3 fatty acids of between 5:1 to 1:5.

DETAILED DESCRIPTION

For a complete understanding of the present disclosure and the advantages thereof, reference is made to the following detailed description, taken in conjunction with the accompanying figures.

It should be appreciated that various aspects of the present disclosure disclosed herein are merely illustrative of specific ways to make and use the disclosure and do not limit the scope of the disclosure when taken into consideration with the appended claims, the detailed description and the accompanying figures.

It is to be appreciated that features from one aspect of the disclosure will be apparent to those skilled in the art from a consideration of the description or examples of the disclosure disclosed herein and those features can be combined with features from other aspects/embodiments of the present disclosure.

As used in this disclosure and the appended claims, the singular forms "a", "an" and "the" include plural referents unless the context clearly specifies otherwise.

The present inventors have developed a nutritional composition for inflammatory bowel disease (e.g. Crohn's disease).

The term "nutritional composition" includes, but is not limited to, complete nutritional compositions, partial or incomplete nutritional compositions, and disease or condition specific nutritional compositions. A complete nutritional composition (i.e., those which contain all the essential macro and micro nutrients) can be used as a sole source of nutrition for the patient. Patients can receive 100% of their nutritional requirements from such complete nutritional composition. A partial or incomplete nutritional composition does not contain all the essential macro and micro nutrients and cannot be used as a sole source of nutrition for the patient. Partial or incomplete nutritional compositions can be used as a nutritional supplement. A disease or condition specific nutritional composition is a composition that delivers nutrients or pharmaceuticals and can be a complete or partial nutritional composition.

It has been found that the nutritional composition when used during an active phase of inflammatory bowel disease (e.g. Crohn's disease): can induce remission (as indicated by a PCDAI score and endoscopic assessments, can down regulate the inflammatory response, promote gut mucosal healing, can promote weight gain, can promote linear growth and improve nutritional status as well as improving musculoskeletal alterations.

Figure 1:
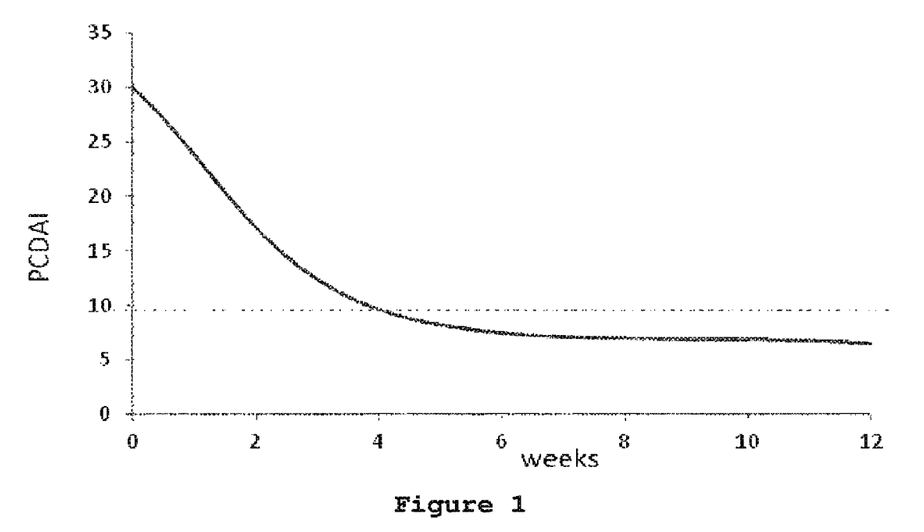
FIG. 1 shows a Pediatric Crohn's Disease Activity Index (PCDAI) in children aged between 6.6-17.7 years with Crohn's disease when administered with a nutritional composition according to the present disclosure.

The PCDAI score is well known in the art and PCDAI refers to Pediatric Crohn's Disease Activity Index. PCDAI is a reliable and validated multi-parameter measure which classifies disease activity amongst children and adolescents. It is found that the nutritional composition of the present disclosure significantly reduces the PCDAI in the first two weeks of treatment—reducing to the minimum value within 8 weeks as depicted in FIG. 1.

The nutritional composition comprises acid casein protein, vitamin K in a ratio of vitamin K1:K2 being between 3:1 to 1:3 and the vitamin K present in an amount of between 17.5 to 100 µg/100 g of the nutritional composition, vitamin D present in an amount of between 2.5 to 75 µg/100 g of the nutritional composition; and n6/n3 fatty acids in a ratio of n6:n3 fatty acids of between 5:1 to 1:5.

Acid casein is produced by acidifying milk until the isolectric point of casein is reached (at pH 4.7). Subsequently, the so-called acid casein protein precipitates. The process is well established in the art (see background section of U.S. Pat. No. 4,397,926). Often, acid casein is obtained in a process of continued casein coagulation from accurately skimmed milk under the influence of sour whey. However, other production methods are available.

Acid casein protein is high in naturally occurring transforming growth factor Beta-2 (TGF-β2). Transforming growth factor Beta-2 (TGF-β2) is an anti-inflammatory cytokine which plays an important role in gut mucosal healing.

Vitamin K denotes a group of lipophilic, hydrophobic and essential vitamins having a common chemical ring structure (napthoquinone). Vitamin K1 is a single compound known as phylloquinone or phytomenadione and vitamin K2 is a series of vitamins known as menaquinones or menatetrenones.

As noted inflammatory bowel disease (e.g., Crohn's disease) is known to compromise bone growth, bone quality and ultimately bone density. An incidence of low bone mass in patients having inflammatory bowel disease (e.g., Crohn's disease) ranges from about 30-50%. Vitamin K is usually deficient in patients having inflammatory bowel disease (e.g., Crohn's disease) and the consequential limited bioavailability may reduce osteocalcin carboxylation during bone mass formation as well as reduce bone strength, bone mineralization and bone micro-architecture. Accordingly patients having inflammatory bowel disease (e.g., Crohn's disease) benefit from a more effective dose of vitamin K. Low vitamin K levels can lead to an increase in the rate of bone resorption, without a compensatory increase in the rate of bone formation.

Rather than attempting to increase the intake levels via higher vitamin K1 intake, Vitamin K2 allows for a more potent form of vitamin K without negatively impacting parameters of anticoagulation. Vitamin K2, compared to vitamin K1 provides enhanced absorption and more stable serum levels through a longer half-life when compared to vitamin K1. The enhanced absorption of vitamin K2 to extraheptic tissue allows for a greater impact for improving musculoskeletal health in patients with inflammatory bowel disease (e.g. Crohn's Disease).

The present applicant has surprisingly found that administering vitamin K in a ratio of vitamin K1:K2 being between 3:1 to 1:3 and the vitamin K present in an amount of between 17.5 to 100 µg/100 g of the nutritional composition as part of the nutritional composition improves osteocalcin carboxylation and improves indices of bone health during normal growth and development in children. Additionally, vitamin K supplementation also promotes bone growth and bone quality in patients with inflammatory bowel disease (e.g. Crohn's Disease). The nutritional composition when administered increases bone density and improves bone tissue micro-architecture in patients with inflammatory bowel disease (e.g. Crohn's Disease), thereby reducing the incidence for fracture risk. The effects of vitamin K is seen directly on bone quality such that this form of vitamin K modulates formation of proteins in the organic matrix of the bone involved in micro-architectural morphology, mineralization, density, elasticity and mechanical stiffness, as measured by peripheral quantitative computer tomography ("pQCT") or Dual Energy X-ray absorptiometry ("DEXA").

Bone density is expressed as the relationship between bone mass (expressed as the degree of photon attenuation through the bone, or bone mineral content (BMC)) and the image of the bone on a film (i.e., the area) (expressed as $BMC/cm^2$). Additionally, pQCT is a procedure that evaluates peripheral bone in 3 dimensions (volumetric) and is commonly applied to the forearm or tibia. A radiation source (typically x-rays) and a sensor revolves around the bone under examination, which is then reconstructed on the computer screen in a three-dimensional image. pQCT is an optimal technique for evaluating bone geometry even though sensitivity varies with the site under evaluation. Unlike most other techniques, pQCT measures true bone density (volumetric mineral bone density) because it normalizes the bone mineral content derived not from the projected area but rather from the volume of the examined bone. pQCT can also be used to calculate the SSI, an index of bone resistance to torsion. The index takes into account bone geometry and the bone's mineral characteristics. See, Geometry and bone density, Radetti, G., et al., Panminerva Med 2006; 48: 181-6.

DEXA is based on x-ray spectrometry and its fundamental principle is based on the degree of attenuation of x-rays emitted from 2 different sources of energy. DEXA is normally used to evaluate lumbar or proximal femoral bone mineralization. DEXA has an accuracy of 4-10% and a coefficient of variation of 1-1.5%.

In a preferred embodiment vitamin K is present in an amount of vitamin K in a ratio of vitamin K1:K2 being between 2:1 to 1:2.

In a preferred embodiment vitamin K is present in an amount of vitamin K in a ratio of vitamin K1:K2 being 1:1.

In a preferred embodiment, vitamin K is present in an amount of between 20 to 50 µg/100 g of the nutritional composition.

In a preferred embodiment, vitamin K is present in an amount of between 20 to 40 µg/100 g of the nutritional composition.

In a preferred embodiment, vitamin K is present in an amount of between 22 to 30 µg/100 g of the nutritional composition.

In a preferred embodiment, vitamin K is present in an amount of between 25 to 30 µg/100 g of the nutritional composition.

In a preferred embodiment, vitamin K is present in an amount of between 26 to 28 µg/100 g of the nutritional composition.

In a preferred embodiment, vitamin K is present in an amount of 27/100 g of the nutritional composition.

Vitamin D is an important nutrient for the development of the inorganic matrix of the bone. The vitamin D is present in an amount of between 2.5 to 75 µg/100 g of the nutritional composition.

In a preferred embodiment vitamin D is present in an amount of between 7.5 to 70 µg/100 g of the nutritional composition.

In a preferred embodiment vitamin D is present in an amount of between 7.5 to 15 µg/100 g of the nutritional composition.

In a preferred embodiment vitamin D is present in an amount of between 10 to 13 µg/100 g of the nutritional composition.

In a preferred embodiment vitamin D is present in an amount of between 11 to 12 µg/100 g of the nutritional composition.

In a preferred embodiment vitamin D is present in an amount of 11.6 µg/100 g of the nutritional composition.

Figure 2:
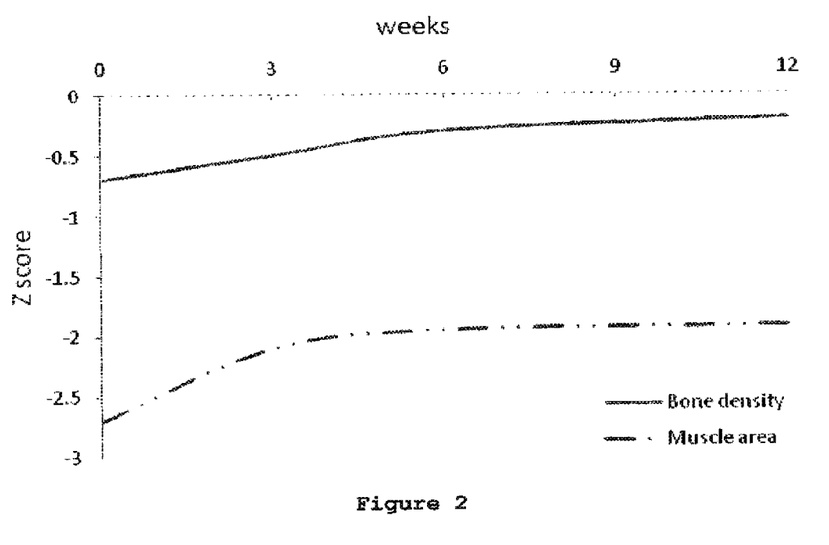
FIG. 2 shows the effects of the nutritional composition of the present disclosure on bone density and muscle cross sectional area when administered to children aged between 6.6-17.7 years with Crohn's disease.

FIG. 2 shows that administration of the nutritional composition by enteral feeding during 12 weeks significantly improves bone density in children aged between 6.6-17.7 years old with inflammatory bowel disease (e.g. Crohn's Disease).

Furthermore the nutritional composition has enhanced anti-inflammatory activity for mucosal healing due to the presence of the n6/n3 fatty acids and/or mixtures thereof. The n6/n3 fatty acids are present in a ratio of n6:n3 fatty acids of between 5:1 to 1:5. Since the nutritional composition promotes mucosal healing, there is an improvement in the absorption of nutrients in a patient with inflammatory bowel disease (e.g., Crohn's disease).

Examples of the n3 omega-fatty acids are hexadecatrienoic acid (HTA) C16:3, alpha-linolenic acid (ALA) C18:3, stearidonic acid (SDA) C18:4, eicosatrienoic acid (ETE) C20:3, eicosatetraenoic acid (ETA) C20:4, eicosapentaenoic acid (EPA) C20:5, heneicosapentaenoic acid (HPA) C21:5, docosapentaenoic acid (DPA) C22:5, docosahexaenoic acid (DHA) C22:6, tetracosapentaenoic acid C24:5 and tetracosahexaenoic acid C24:6.

In a preferred embodiment the n3 omega-3-fatty acids are eicosapentaenoic acid (EPA) C20:5 and docosahexaenoic acid (DHA) C22:6.

The n3 omega-3-fatty acids can be derived from fish oils, algal oil, squid oil, and plant oils such as echium oil and flaxseed oil and/or mixtures thereof.

Examples of the n6, omega-6-fatty acid are linolenic acid (LA) C18:2, gamma-linolenic acid (GLA) C18:3, eicosadienoic acid C20:2, dihomo-gamma-linolenic acid (DGLA) C20:3, arachidonic acid (AA) C20:4, docosadienoic acid C22:2, adrenic acid C22:4, docosapentaenoic acid C22:5, tetracosatetraenoic acid C24:4, tetracosapentaenoic acid C24:5 and Calendic acid C18:3.

The n6 omega-6-fatty-acids can be derived from poultry, eggs, avocado, nuts, cereals, durum wheat, whole-grain, vegetable oils, evening primrose oil, borage oil, blackcurrant seed oil, flax/linseed oil, rapeseed oil, canola oil, hemp oil, soybean oil, cottonseed oil, sunflower seed oil, corn oil, safflower oil, pumpkin seeds, acai berry, cashews and spirulina and/or mixtures thereof.

In a preferred embodiment n3, omega-3-fatty acid is alpha-linolenic acid (ALA) C18:3 and the n6, omega-6-fatty acid is linolenic acid (LA) C18:2.

FIG. 2 shows that administration of the nutritional composition by enteral feeding during 12 weeks significantly improves muscle cross-sectional area in children aged between 6.6-17.7 years old with inflammatory bowel disease (e.g. Crohn's Disease).

The nutritional composition may further include one or more amino acids. Non-limiting examples of amino acids include Alanine, Arginine, Asparagine, Aspartate, Citrulline, Cysteine, Glutamate, Glutamine, Glycine, Histidine, Eydroxyproline, Hydroxyserine, Hydroxytyrosine, Hydroxylysine, Isoleucine, Leucine, Lysine, Methionine, Phenylalanine, Proline, Serine, Taurine, Threonine, Tryptophan, Tyrosine, Valine, HICA (Alpha-Hydroxyisocaproic Acid), HIVA (Alpha-Hydroxyisovaleric Acid), HIMVA (alpha-hydroxymethylvaleric acid) or a combination thereof.

In a further embodiment the nutritional composition may comprise minerals such as sodium, potassium, calcium, phosphorus, magnesium, chloride, iron, zinc, copper, manganese, fluoride, chromium, molybdenum, selenium, iodine or any combination thereof.

In a further embodiment the nutritional composition comprises further vitamins such as Vitamin A, Vitamin E, Vitamin C, Vitamin B1, Vitamin B2, Pantothenic Acid, Vitamin B6, Vitamin B12, Niacin, Folic Acid, Biotin and Choline or any combination thereof.

In a further embodiment, the nutritional composition further includes one or more prebiotics. As used herein, a prebiotic is a selectively fermented ingredient that allows specific changes, both in the composition and/or activity in the gastrointestinal microflora, which confers benefits upon host well-being and health. Non-limiting examples of prebiotics include fructooligosaccharides, inulin, lactulose, galactooligosaccharides, acacia gum, soyoligosaccharides, xylooligosaccharides, isomaltooligosaccharides, gentiooligosaccharides, lactosucrose, glucooligosaccharides, pecticoligosaccharides, guar gum, partially hydrolyzed guar gum, sugar alcohols, alpha glucan, beta glucan, or a combination thereof.

In a further embodiment, the nutritional composition further includes one or more probiotics. As probiotics are preferably microorganisms (alive, including semi-viable or weakened, and/or non-replicating), metabolites, microbial cell preparations or components of microbial cells that could confer health benefits on the host when administered in adequate amounts, more specifically that beneficially affect a host by improving its intestinal microbial balance, leading to effects on the health or well-being of the host. In general, it is believed that these probiotics inhibit and/or influence the growth and/or metabolism of pathogenic bacteria in the intestinal tract. The probiotics may also activate the immune function of the host. Non-limiting examples of probiotics include *Saccharomyces, Debaromyces, Candida, Pichia, Torulopsis, Aspergillus, Rhizopus, Mucor, Penicillium, Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus, Lactobacillus* or a combination thereof.

In a further embodiment the nutritional compositions further comprises a synbiotic. The synbiotic is a supplement that contains both prebiotic(s) and probiotic(s). The prebiotic(s) and the probiotic(s) work together to improve the micro flora of the intestine. The synbiotic comprises any combination of the prebiotic(s) and the probiotic(s) referred to above.

In a further embodiment the nutritional composition comprises a pharmaceutically acceptable carrier and/or flavor agent and/or colorants. The use of a flavor agent provides a flavor to the nutritional composition that makes the nutritional composition more palatable to patients with inflammatory bowel disease (e.g. Crohn's Disease).

In a preferred embodiment the nutritional composition is in the form of a powder that is to be reconstituted with a liquid.

The nutritional composition can be in an administrable form such as pharmaceutical formulations, nutritional formulations, tube-feed formulations, dietary supplements, functional foods, beverage products or a combination thereof.

As used herein, a "tube feed" formulation is preferably a complete or incomplete nutritional product that is administered to a patients gastrointestinal tract, other than through oral administration, including but not limited to a nasogastric tube, orogastric tube, gastric tube, jejunostomy tube (J-tube), percutaneous endoscopic gastrostomy (PEG), port, such as a chest wall port that provides access to the stomach, jejunum and other suitable access ports.

The nutritional composition of the present disclosure is advantageous in patients with inflammatory bowel disease (e.g. Crohn's Disease) who wish to avoid treatment with drug therapy and avoid side effects that are associated with drug therapy.

The nutritional composition of the present disclosure can be used in patients with inflammatory bowel disease (e.g. Crohn's Disease) as a supplement to drug therapy.

The nutritional composition of the present disclosure is advantageous in patients with inflammatory bowel disease (e.g. Crohn's Disease) who fail to respond to medication.

Example

The nutritional composition according to the present disclosure was manufactured according to table 1.

The column "Example of nutritional composition—Constituent per 100 g" shows an example of the nutritional composition based on the constituents of the nutritional composition per 100 g of the nutritional composition, when the nutritional composition is in the form of a powder.

The column "Declared value per serving: 20.4 g of the nutritional composition (powder) per 84 ml water to form 100 ml reconstituted formula" shows the nutritional composition based on the constituents of the nutritional composition when 20.4 g of the example of the nutritional composition is reconstituted with 84 ml of water to form a 100 ml nutritional composition in the form of a liquid.

TABLE 1

| Constituent of nutritional composition | Quantity Units | Example of nutritional composition-Constituent per 100 g. | Declared value per serving: 20.4 g of the nutritional composition (powder) per 84 ml water to form 100 ml reconstituted formula | Declared value quantity/ 100 kcal | FSMP min 100 kcal | FSMP max 100 kcal |
|---|---|---|---|---|---|---|
| Energy kcal | | 493 | | 100 | | |
| kJ | | 2067 | | 419 | | |
| Protein casein (14% AET) | g | 17.5 | 3.6 | 3.5 | | |
| Carbohydrates (44% AET) | g | 54 | 11.0 | 11.0 | | |
| Of which | | | | | | |
| sugars | g | 0 | 0.0 | 0.0 | | |
| lactose | g | 0 | 0.0 | 0.0 | | |
| Lipids (42% AET) | g | 23 | 4.7 | 4.7 | | |
| Medium chain triglycerides | g | 5.7 | 1.2 | 1.2 | | |
| Saturated fatty acids | g | 7.00 | 1.4 | 1.4 | | |
| Mono saturated fatty acids | g | 9.28 | 1.9 | 1.9 | | |
| Poly saturated fatty acids | g | 4.54 | 0.9 | 0.9 | | |
| Alpha-linolenic Acid C18:3 n-3 | g | 0.66 | 0.1 | 0.1 | | |
| linolenic acid C18:2 n-6 | g | 3.6 | 0.7 | 0.7 | | |
| Fibres (0% AET) | g | 0 | 0.0 | 0.0 | | |
| Minerals | | | | | | |
| Sodium | mg | 200 | 40.8 | 40.6 | 30 | 175 |
| Potassium | mg | 750 | 153.0 | 152.1 | 80 | 295 |
| Calcium | mg | 600 | 122.4 | 121.7 | 35 | 250 |
| Phosphorus | mg | 390 | 79.6 | 79.1 | 30 | 80 |
| Magnesium | mg | 100 | 20.4 | 20.3 | 7.5 | 25 |
| Chloride | mg | 390 | 79.6 | 79.1 | 30 | 175 |
| Iron | mg | 5.40 | 1.10 | 1.10 | 0.5 | 2 |
| Zinc | mg | 3.40 | 0.69 | 0.69 | 0.5 | 1.5 |
| Copper | mg | 0.4 | 0.08 | 0.08 | 0.06 | 0.5 |
| Manganese | μg | 980 | 199.9 | 198.8 | 50 | 500 |
| Fluoride | mg | 0 | 0.0 | 0.0 | 0 | 0.20 |
| Chromium | μg | 22 | 4.49 | 4.46 | 1.25 | 15 |
| Molybdenum | μg | 35 | 7.14 | 7.10 | 3.5 | 18 |
| Selenium | μg | 30 | 6.12 | 6.09 | 2.5 | 10 |
| Iodine | μg | 49 | 10.0 | 9.9 | 6.5 | 35 |
| Vitamins | | | | | | |
| Vitamin A, TOTAL | μg | 410 | 83.6 | 83.2 | 35.0 | 180 |
| Vitamin A (beta carotene) | μg | 140 | 28.6 | 28.4 | | |
| Vitamin A (retinol) | μg | 270 | 55 | 54.8 | | |
| Vitamin D | μg | 11.6 | 2.4 | 2.4 | 0.5 | 3 |
| Vitamin E | mg | 6.5 | 1.3 | 1.3 | 0.50 | 3.00 |
| Vitamin K (K1:K2 1:1) | μg | 27 | 5.5 | 5.5 | 3.5 | 20 |
| Vitamin C | mg | 47 | 9.6 | 9.5 | 2.25 | 22 |
| Vitamin B1 | mg | 0.6 | 0.1 | 0.1 | 0.06 | 0.5 |
| Vitamin B2 | mg | 0.60 | 0.1 | 0.1 | 0.08 | 0.5 |
| Pantothenic Acid | mg | 2.4 | 0.5 | 0.5 | 0.15 | 1.5 |
| Vitamin 86 | mg | 0.800 | 0.2 | 0.2 | 0.08 | 0.5 |

TABLE 1-continued

| Constituent of nutritional composition | Quantity Units | Example of nutritional composition- Constituent per 100 g. | Declared value per serving: 20.4 g of the nutritional composition (powder) per 84 ml water to form 100 ml reconstituted formula | Declared value quantity/ 100 kcal | FSMP min 100 kcal | FSMP max 100 kcal |
|---|---|---|---|---|---|---|
| Vitamin B12 | µg | 1.5 | 0.3 | 0.3 | 0.07 | 0.7 |
| Niacin | mg | 7.8 | 1.6 | 1.6 | 0.9 | 3 |
| Folic Acid | µg | 120 | 24.5 | 24.3 | 10 | 50 |
| Biotin | µg | 16 | 3.3 | 3.2 | 0.75 | 7.5 |
| Choline | mg | 150 | 30.6 | 30.4 | | |

(The "," in the above table are decimal points and are thus interpreted to be "." in those regions of the world where "." are used to indicate decimal points, like in the USA.)

The reconstituted nutritional formulation was administered to children aged between 6.6-17.7 years old with inflammatory bowel disease (e.g. Crohn's Disease) over a period of twelve weeks.

After noting baseline characteristics, the children aged between 6.6-17.7 years old with inflammatory bowel disease (e.g. Crohn's Disease) were administered the nutritional composition for 4 weeks as sole nutritional support to achieve clinical remission. Administration was then continued for 8 weeks.

The children aged between 6.6-17.7 years old with inflammatory bowel disease (e.g. Crohn's Disease) were followed up at 4 and 12 weeks after the first visit. Muscle cross sectional area and bone density was measured at the first visit and at 12 weeks.

A plasma metabolic profile of the children aged between 6.6-17.7 years old with inflammatory bowel disease (e.g. Crohn's Disease) was obtained at the first visit and after 4 weeks of nutritional intervention by a metabonomics approach. The metabonomics approach consisted of using a Biocrates Life Sciences AbsoluteIDQ™ kit according to the manufacturer's instructions. The plasma metabolic profile of the children aged between 6.6-17.7 years old with inflammatory bowel disease (e.g. Crohn's Disease) was processed with multivariate statistics to identify metabolic information (biomarkers). The metabolic information (biomarkers) is indicative of the physiological status of the children aged between 6.6-17.7 years old with inflammatory bowel disease (e.g. Crohn's Disease) in response of to the intervention with the nutritional composition. Metabolic trajectories of the plasma metabolic profile were observed over time, which were associated with distinct differences in circulating amino acids and lipids.

Significant differences were observed.

It was observed that a 4 week intervention with the nutritional composition is able to partially restore a metabolic profile in the children aged between 6.6-17.7 years old with inflammatory bowel disease (e.g. Crohn's Disease). The initial profiling of amino acid and lipids in the children aged between 6.6-17.7 years old with inflammatory bowel disease (e.g. Crohn's Disease) at the first visit compared to age-matched controls demonstrates a significant reduction in a number of metabolites.

The 4 week intervention with the nutritional composition is not only able to induce remission of an acute episode effect of inflammatory bowel disease, but also surprisingly restores the levels of amino acids threonine, histidine and tryptophan. In addition, definitive trends for restoration of the amino acids proline and glutamine were also observed. Hence the nutritional composition may further comprise amino acids to mirror restoration of the levels of amino acids found in a patient in a state of remission of an acute episode effect of inflammatory bowel disease.

Apart from a protein catabolic response, a reduction in various lipid species from the first visit was also observed when compared to age-matched controls. Similar to the amino acid response, nutritional intervention is able to restore the anabolic response in multiple lipid metabolites after 4 weeks. The results indicate that the nutritional composition can switch the catabolic response to an anabolic response.

It has also been found that the nutritional composition of the present disclosure significantly reduces the PCDAI (Pediatric Crohn's Disease Activity Index) in the first four weeks of treatment—reducing to the minimum value within 8 weeks as depicted in FIG. 1.

Furthermore, since muscle breakdown is thought to contribute to the concentration of plasma amino acids, nutritional intervention which restores these amino acids as described above, will reduce muscle catabolic stress. In order to demonstrate this effect, a Z score for the muscle cross-sectional area at the first visit and after 12 weeks was established. The Z-score measures the change in muscle cross-sectional area as compared to a reference population. As shown in FIG. 2, a 4 week intervention with the nutritional composition is able to alleviate loss of muscle cross-sectional area and promote muscle cross-sectional area within 12 weeks.

Thus it is demonstrated that an nutritional intervention in the children aged between 6.6-17.7 years old with inflammatory bowel disease (e.g. Crohn's Disease) is able to correct a metabolic disruption and thereby alleviate the catabolic response in the muscle and alleviate inflammatory bowel disease (e.g. Crohn's Disease) associated musculoskeletal changes.

Furthermore it was noted that administration of the nutritional composition in maintenance therapy leads to significantly longer time to relapse. Therefore the nutritional composition promotes longer remission periods with improved muscle cross-sectional area and improved bone density during a remission phase in patients with inflammatory bowel disease (e.g. Crohn's Disease).

It has been surprisingly found out that the quantities of the components used with ratios within the above ranges play an important role and are advantageous when the composition is used in patients with inflammatory bowel disease. The nutritional composition promotes and improves muscle cross-sectional area and bone density, the nutritional composition also leads to significantly longer time to relapse in patients with inflammatory bowel disease.

Having thus described the present disclosure in detail and the advantages thereof, it is to be understood that the forgoing detailed description of the disclosure is not intended to limit the scope of the disclosure thereof.

The person skilled in the art will be able to practice the disclosure by combining various aspects and embodiments. The disclosure is not limited to the detailed description and and/or the examples.

What is desired to be protected by letters patent is set forth in the following claims.

The invention is claimed as follows:

1. A method of improving musculoskeletal health in patients, the method comprising:
administering to a patient in need of same a nutritional composition comprising acid casein protein, vitamin K at a ratio of vitamin K1:K2 between 3:1 to 1:3 and the vitamin K present in an amount of between 17.5 to 100 μg/100 g of the nutritional composition, vitamin D present in an amount of between 2.5 to 75 μg/100 g of the nutritional composition, and n6/n3 fatty acids at a ratio of n6:n3 fatty acids between 5:1 to 1:5.

2. The method of claim 1, wherein the improving musculoskeletal health is improved bone density.

3. The method of claim 1, wherein the improving musculoskeletal health is improved muscle cross-sectional area.

4. The method of claim 1, wherein the nutritional composition is in an administrable form selected from the group consisting of a pharmaceutical formulation, a nutritional formulation, a tube-feed formulation, a dietary supplement, a functional food, a beverage product and combinations thereof.

5. The method of claim 1, wherein the nutritional composition is a complete nutritional composition.

6. The method of claim 1, wherein the n6 fatty acids are selected from the group consisting of linolenic acid (LA) C18:2, gamma-linolenic acid (GLA) C18:3, eicosadienoic acid C20:2, dihomo-gamma-linolenic acid (DGLA) C20:3, arachidonic acid (AA) C20:4, docosadienoic acid C22:2, adrenic acid C22:4, docosapentaenoic acid C22:5, tetracosatetraenoic acid C24:4, tetracosapentaenoic acid C24:5, calendic acid C18:3, and mixtures thereof.

7. The method of claim 1, wherein the n3 fatty acids are selected from the group consisting hexadecatrienoic acid (HTA) C16:3, alpha-linolenic acid (ALA) C18:3, stearidonic acid (SDA) C18:4, eicosatrienoic acid (ETE) C20:3, eicosatetraenoic acid (ETA) C20:4, eicosapentaenoic acid (EPA) C20:5, heneicosapentaenoic acid (HPA) C21:5, docosapentaenoic acid (DPA) C22:5, docosahexaenoic acid (DHA) C22:6, tetracosapentaenoic acid C24:5, tetracosahexaenoic acid C24:6, and mixtures thereof.

8. The method of claim 1, wherein the nutritional composition further comprises one or more amino acids selected from the group consisting of Alanine, Arginine, Asparagine, Aspartate, Citrulline, Cysteine, Glutamate, Glutamine, Glycine, Histidine, Hydroxyproline, Hydroxyserine, Hydroxytyrosine, Hydroxylysine, Isoleucine, Leucine, Lysine, Methionine, Phenylalanine, Proline, Serine, Taurine, Threonine, Tryptophan, Tyrosine, Valine, HICA (Alpha-Hydroxyisocaproic Acid), HIVA (Alpha-Hydroxyisovaleric Acid), HIMVA (alpha-hydroxymethylvaleric acid) and combinations thereof.

9. The method of claim 1, wherein the nutritional composition further comprises one or more additional vitamins selected from the group consisting Vitamin A, Vitamin E, Vitamin C, Vitamin B1, Vitamin B2, Pantothenic Acid, Vitamin B6, Vitamin B12, Niacin, Folic Acid, Biotin, and Choline, and combinations thereof.

* * * * *